United States Patent
Wen et al.

[11] Patent Number: 6,001,392
[45] Date of Patent: Dec. 14, 1999

[54] ANTITUSSIVE DRUGS DELIVERED BY ION EXCHANGE RESINS

[75] Inventors: Betty Wen, Scarborough; Michael P. Ramsay, Ajax; Heinrich Scheurer, Scarborough; Val Dokuzovic, Mississauga; Vincent Lam, Markham, all of Canada

[73] Assignee: Warner-Lambert Company, Morris Plains, N.J.

[21] Appl. No.: 08/994,406

[22] Filed: Dec. 19, 1997

[51] Int. Cl.⁶ .............................. A61K 9/10; A61K 47/30
[52] U.S. Cl. .............................................. 424/486; 514/850
[58] Field of Search .................................. 424/486, 457, 424/468; 514/849, 850

[56] References Cited

U.S. PATENT DOCUMENTS

| | | |
|---|---|---|
| 4,221,778 | 9/1980 | Raghunathan . |
| 4,762,709 | 8/1988 | Sheumaker . |
| 4,780,322 | 10/1988 | Martani et al. . |
| 4,788,055 | 11/1988 | Fischer et al. . |
| 4,847,077 | 7/1989 | Raghunathan . |
| 4,859,461 | 8/1989 | Chow et al. . |
| 4,859,462 | 8/1989 | Chow et al. . |
| 4,894,239 | 1/1990 | Nonomura et al. . |
| 4,983,401 | 1/1991 | Eichel et al. . |
| 4,996,047 | 2/1991 | Kelleher et al. . |
| 4,999,189 | 3/1991 | Kogan et al. . |
| 5,026,559 | 6/1991 | Eichel et al. . |
| 5,186,930 | 2/1993 | Kogan et al. . |
| 5,275,820 | 1/1994 | Chang . |
| 5,288,503 | 2/1994 | Wood et al. . |
| 5,296,228 | 3/1994 | Chang et al. . |

FOREIGN PATENT DOCUMENTS

| | | |
|---|---|---|
| 0225615 | 6/1987 | European Pat. Off. . |
| 0367746 | 5/1990 | European Pat. Off. . |
| 0565301 | 10/1993 | European Pat. Off. . |
| WO9113612 | 9/1991 | WIPO . |
| WO9210171 | 6/1992 | WIPO . |
| WO9211038 | 7/1992 | WIPO . |
| WO9211871 | 7/1992 | WIPO . |

OTHER PUBLICATIONS

Influence of Wax Coatings on Release Rate of Anions from Ion–Exchange Resin Beads, S. Motycka and J.G. Nairn. Journal of Pharmaceutical Sciences, vol. 67, No. 4, Apr. 1978: pp. 500–503.

Preparation and Evaluation of Microencapsulated Ion–Exchange Beads, S. Motycka and J.G. Nairn, Journal of Pharmaceutical Sciences, vol. 68, No. 2, Feb. 1979: pp. 211–214.

*Primary Examiner*—Edward J. Webman
*Attorney, Agent, or Firm*—Evan J. Federman

[57] ABSTRACT

The present invention relates generally to a mixture of coated and non-coated sulfonic acid cation exchange resins (Amberlite IR69) cross-linked with about 8% divinyl benzene onto which dextromethorphan has been loaded. About 30% of the drug/resin complexes are coated with a mixture of ethyl cellulose or ethyl cellulose latexes with plasticizers and water dispersible polymers such as SURELEASE. The coating level is about 50% w/w drug. Coated and uncoated drug/resin complexes are loaded with drug to about 45% by weight drug/resin complex. The ratio of coated and uncoated drug/resin complexes is about 55/45. The particle sizes of the coated and uncoated drug/resin complexes is about 20 to about 300 and about 20 to about 250 microns, respectively.

18 Claims, 1 Drawing Sheet

6,001,392

ANTITUSSIVE DRUGS DELIVERED BY ION EXCHANGE RESINS

FIELD OF THE INVENTION

The present invention relates generally to a controlled-release syrup suspension for oral administration, preferably containing a dextromethorphan polystyrene sulfonate resin. The composition provides up to 12 hours of symptomatic relief from dry coughing.

BACKGROUND OF THE INVENTION

Dextromethorphan is an antitussive used in many over-the-counter cold medications. It has an opioid-like structure but, being a d-isomer, it does not possess the analgesic or addicveti retes of opioids. It acts centrally to relieve cough, similarly as opioids. It is active against dry cough and does not exhibit significant expectorant properties for productive cough.

As is well known, the maximum time of effectiveness in dextromethorphan compositions is only a few hours because of biological modification and/or elimination of the medication in the body (i.e., the usual doses for immediate-release formulations range from 15–30 mg every 4–6 hours). Consequently, repeated dosages must be taken at frequent intervals to obtain long term therapeutic levels of drug. Furthermore, this drug usually dissolves readily in the digestive juices and the total dosage is immediately fed into the blood stream. After high initial peak concentrations, the level of drug in the blood stream constantly decreases because of the biological elimination, so there is little or no therapeutic effect at the end of the period between dosages. As a result, the therapeutic effect fluctuates between dosages corresponding to the peaks and valleys in the level of drug in the blood as commonly measured by trough to peak ratios.

It is possible to incorporate materials into dextromethorphan compositions in such a manner that the dextromethorphan is liberated from the compositions at a predetermined rate. In this way, it is possible, for example, to achieve a prolongation of the period of action and thus to avoid too quick and/or too concentrated a release of the dextromethorphan and too high peaks of the blood or tissue levels, which can lead to undesirable side effects. DELSYM DM, marketed by Ciba Pharmaceuticals, is an example of a sustained-release dextromethorphan composition. The sustained-release characteristics of the composition are achieved by use of small particles of an ion-exchange resin bound to the dextromethorphan which delay release of the drug in the gastrointestinal tract.

While sustained-release of dextromethorphan is achieved by compositions such as DELSYM DM, certain advances to this area of technology are required. The bioavailability of dextromethorphan from these type of compositions is relatively low due to the strong bond between residual amounts of dextromethorphan and the ion exchange resin. The total percentage of dextromethorphan released from dextromethorphan/ion exchange resin complexes is incomplete, and under certain in vitro conditions it has been observed that even after a twelve hour period of time, about 20% of dextromethorphan remains bound to the ion exchange resin.

It is an object of the present invention to provide a sustained-release antitussive liquid formulation.

A further object of the present invention is to provide a sustained-release antitussive liquid formulation which is not dependent on the presence of large amounts of drug/resin complexes.

Another object of the present invention is to provide a sustained-release antitussive liquid formulation which is capable of demonstrating a release profile which will result in up to a twelve hour cough relief

SUMMARY OF THE INVENTION

Surprisingly and unexpectedly, these and other objectives, which are apparent from the following, have now been realized with a sustained-release antitussive composition comprising in a preferred embodiment, a mixture of coated and non-coated sulfonic acid cation exchange resins (Amberlite IRP-69) cross-linked with preferably about 8% divinyl benzene onto which dextromethorphan has been loaded. About 30% of the drug/resin complexes are coated with a mixture of ethyl cellulose or ethyl cellulose latexes with plasticizers and water dispersible polymers such as SURELEASE. The coating level is about 50% w/w of the drug/resin complex. Coated and uncoated drug/resin complexes are loaded with drug to about 30 to about 50% w/w drug. The ratio of coated and uncoated drug/resin complexes is about 55/45. The particle sizes of the coated and uncoated drug/resin complexes are about 20 to about 300 and about 20 to about 250 um, respectively.

The invention further relates to methods of using the sustained-release compositions in the treatment, management or mitigation of cough, cold, cold-like and/or flu symptoms and the discomfort, pain, fever and general malaise associated therewith.

DETAILED DESCRIPTION OF THE INVENTION

Figure 1:
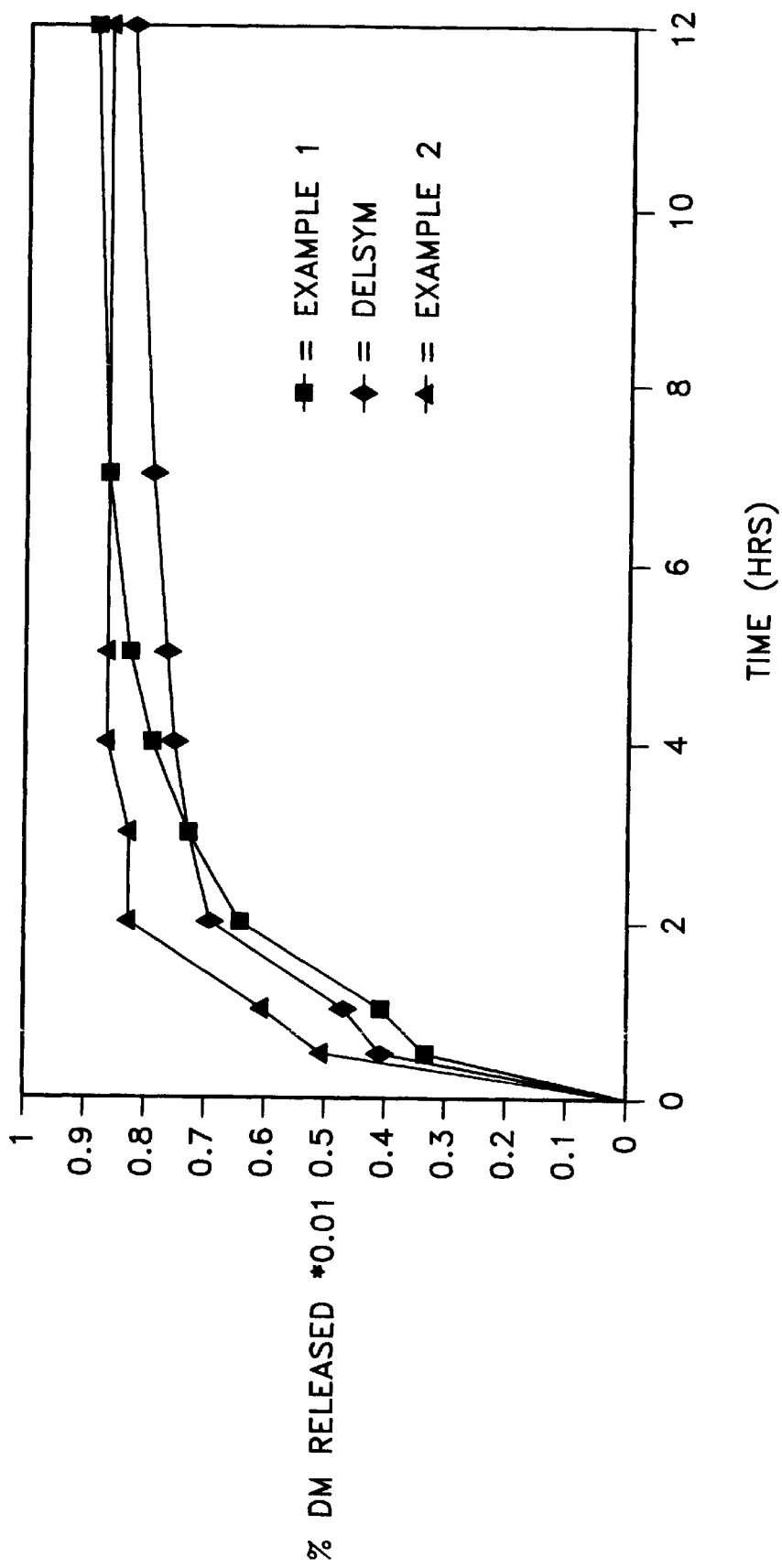
FIG. 1 shows the dissolution profiles of Example 1 and 2 and DELSYM and shows the percent of dextromethorphan HBr $H_2O$ release in hours.

The ion exchange resins suitable for use in these preparations are water-insoluble and consist of a pharmacologically inert organic or inorganic matrix containing covalently bound functional groups that are ionic or capable of being ionized under the appropriate conditions of pH. The organic matrix may be synthetic (e.g., polymers or copolymers of acrylic acid, methacrylic acid, sulfonated styrene, sulfonated divinylbenzene), or partially synthetic (e.g., modified cellulose and dextrans). The inorganic matrix can also be, e.g., silica gel modified by the addition of ionic groups. The covalently bound ionic groups may be strongly acidic (e.g., sulfonic acid), weakly acidic (e.g., carboxylic acid), strongly basic (e.g., quaternary ammonium), weakly basic (e.g., primary amine), or a combination of acidic and basic groups. In general, those types of ion exchangers suitable for use in ion exchange chromatography and for such applications as deionization of water are suitable for use in these controlled release drug preparations. Such ion exchangers are described by H. F. Walton in "Principles of Ion Exchange" (pp. 312–343), incorporated by reference herein. The ion exchange resins useful in the present invention have exchange capacities below about 6 milliequivalents per gram (meq./g) and preferably below about 5.5 meq./g.

The resin is cross-linked with a crosslinking agent selected from difunctional compounds capable of cross-linking polystyrenes; these are commonly known in the art. Preferably, the cross-linking agent is a divinyl or polyvinyl compound. Most preferably the cross-linking agent is divinylbenzene. The resin is cross-linked to an extent of about 3 to about 20%, preferably about 4 to about 16%, more preferably about 6 to about 10%, and most preferably about 8% by weight based on the total resin. The resin is cross-linked with the cross-linking agent by means well known in the art.

The size of the ion-exchange resins should preferably fall within the range of about 20 to about 200 um Particle sizes substantially below the lower limit are difficult to handle in all steps of the processing. Particle sizes substantially above the upper limit, e.g. commercially-available ion-exchange resins having a spherical shape and diameters up to about 1000 um, are gritty in liquid dosage forms and have a greater tendency to fracture when subjected to drying-hydrating cycles. Moreover, it is believed that the increased distance that a displacing ion must travel in its diffusion into these large particles, and the increased distance the displaced drug must travel in its diffusion out of these large particles, cause a measurable but not readily controlled prolongation of release even when the drug/resin complexes are uncoated.

Representative resins useful in this invention include Amberlite IRP-69 (obtained from Rohm and Haas) and Dow XYS-40010.00 (obtained from The Dow Chemical Company). Both are sulfonated polymers composed of polystyrene cross-linked with 8% of divinylbenzene, with an ion exchange capacity of about 4.5 to 5.5 meq./g of dry resin (H+-form). Their essential difference is in physical form. Amberlite IRP-69 consists of irregularly-shaped particles with a size range of 47 to 149 um, produced by milling the parent, large-sized spheres of Amberlite IRP-120. The Dow XYS-40010.00 product consists of spherical particles with a size range of 45 to 150 um. Another useful exchange resin, Dow XYS-40013.00, is a polymer composed of polystyrene cross-linked with 8% of divinylbenzene and functionalized with a quaternary ammonium group; its exchange capacity is normally within the range of approximately 3 to 4 meq./g of dry resin.

The most preferable resin for complexing with antitussives, such as dextromethorphan, is commercially available under the trade name Amberlite IRP-69 (Rohm and Haas).

Adsorption of the drug onto the ion exchange resin particles to form the drug/resin complex is a well known technique as shown in U.S. Pat. Nos. 2,990,332 and 4,221,778. In general the drug is mixed with an aqueous suspension of the resin, and the complex is then washed and dried. Adsorption of drug onto the resin may be detected by measuring a change in the pH of the reaction medium, or by measuring a change in concentration of sodium or drug.

Binding of drug to resin can be accomplished according to four general reactions. In the case of a basic drug, these are: (a) resin (Na-form) plus drug (salt form); (b) resin (Na-form) plus drug (as free base); (c) resin (H-form) plus drug (salt form); and (d) resin (H-form) plus drug (as free base). All of these reactions except (d) have cationic by-products, by competing with the cationic drug for binding sites on the resin, reduce the amount of drug bound at equilibrium. For basic drugs, stoichiometric binding of drug to resin is accomplished only through reaction (d).

Four analogous binding reactions can be carried out for binding an acidic drug to an anion exchange resin. These are: (a) resin (Cl--form) plus drug (salt form); (b) resin (Cl--form) plus drug (as free acid); (c) resin (OH--form) plus drug (salt form); and (d) resin (OH--form) plus drug (as free acid). All of these reactions except (d) have ionic by-products and the anions generated when the reactions occur compete with the anionic drug for binding sites on the resin with the result that reduced levels of drug are bound at equilibrium. For acidic drugs, stoichiometric binding of drug to resin is accomplished only through reaction (d). The binding may be performed, for example, as a batch or column process, as is known in the art.

The drug/resin complex formed is collected and washed with ethanol and/or water to insure removal of any unbound drug. The complexes are usually air-dried in trays at room or elevated temperature.

The drug/resin complex has a ratio of dextromethorphan to resin of about 1:3 to about 3:1, preferably about 1:2 to about 2:1, most preferably about 1:1. The only limit to using ratios in excess of 1:6 is an economic and aesthetic one.

The amount of the drug bonded to the ion exchange resin is in the range from about 25 to about 75% by weight of the drug/resin complex. More preferably, the amount of the drug bonded to the ion exchange resin is in the range from about 33 to about 77% by weight of the drug/resin complex. Most preferably, the amount of the drug bonded to the ion exchange resin is in the range from about 40 to about 60% by weight of the drug/resin complex.

The amount of resinate in the formulation is sufficient to deliver, when administered at one dose every 12 hours, an antitussive effective amount of a drug like dextromethorphan over a period of approximately 12 hours to a patient in need of such administration. A typical adult dose of 10 mL will contain approximately 120 mg of drug/resin complex, i.e. to deliver equivalent to 60 mg of dextromethorphan hydrobromide when the average drug:resin ratio is about 1:1.

The antitussive drugs that are suitable for use in these preparations are acidic, amphoteric or most often basic antitussives. Examples of basic drugs useful in the present invention include, but are not limited to dextromethorphan, diphenhydramine, caramiphen, carbapentane, ethylmorphine, noscapine and codeine.

In the preferred embodiment, the invention relates to pharmaceutical compositions of matter comprising drug/resin complexes having only one active ingredient. In another embodiment, the invention also relates to pharmaceutical compositions of matter comprising the drug/resins in combination with suitable pharmaceutically acceptable non-toxic carriers or excipients, and optionally at least one of an antihistamine, sympathomimetic drug (nasal decongestant, bronchodilator), analgesic, antiinflammatory, cough suppressant and/or expectorant. Compounds which are antihistamines, sympathomimetic drugs (nasal decongestant, bronchodilator), analgesic, antiinflammatory, cough suppressants and/or expectorants are well known to those of skill in the art and need not be discussed in detail herein.

Only a certain percentage of the compositions disclosed herein will contain non-coated drug/resin complexes. The remaining drug/resin complexes are further characterized by the presence of a coating. In the preferred embodiment of the present invention, about 20 to about 80% of the drug/resin complexes in the sustained-release compositions are coated, most preferably about 40 to about 60% of the drug/resin complexes. The coating is a water-permeable, diffusion barrier coating material. The presence of a coating allows one to selectively modify the dissolution profile as desired of a pharmaceutical composition comprising the drug/resin complexes of the present invention.

The coating materials can in general be any of a large number of conventional natural or synthetic film-forming materials used singly, in admixture with each other, and in admixture with plasticizers, pigments, etc. with diffusion barrier properties and with no inherent pharmacological or toxic properties. In general, the major components of the coating should be insoluble in water, and permeable to water and drug. However, it might be desirable to incorporate a water-soluble substance, such as methyl cellulose, to alter the permeability of the coating, or to incorporate an acid-insoluble, base-soluble substance to act as an enteric coating. The coating materials may be applied as a suspension in an aqueous fluid or as a solution in organic solvents. Suitable examples of such coating materials are described by R. C. Rowe in *Materials used in Pharmaceutical Formulation.* (A. T. Florence, editor), Blackwell Scientific Publications, Oxford, 1–36(1984), incorporated by reference herein. Preferably the water-permeable diffusion barrier is selected from the group consisting of ethyl cellulose, methyl cellulose and mixtures thereof Most preferably, the coating material is SURELEASE, manufactured by Colorcon which is water based ethyl cellulose latex, plasticized with dibutyl sebacate or with vegetable oils. Other non-limiting coating materials included within the scope of the present invention are AQUACOAT, manufactured by FMC Corporation of Philadelphia, which is ethylcellulose pseudolatex; solvent based ethylcellulose; shellac; zein; rosin esters; cellulose acetate; EUDRAGITS, manufactured by Rohm and Haas of Philadelphia, which are acrylic resins; silicone elastomers; poly(vinyl chloride) methyl cellulose; and hydroxypropylmethyl cellulose.

Conventional coating solvents and coating procedures (such as fluid bed coating and spray coating) can be employed to coat the particles. Techniques of fluid bed coating are taught, for example, in U.S. Pat. Nos. 3,089,824; 3,117,027; and 3,253,944. The coating is normally applied to the drug/resin complex, but alternatively can be applied to the resin before complexing with the drug. Non-limiting examples of coating solvents include ethanol, a methylene chloride/acetone mixture, coating emulsions, methyl acetone, tetrahydrofuran, carbonetetrachloride, methyl ethyl ketone, ethylene dichloride, trichloroethylene, hexane, methyl alcohol, isopropyl alcohol, methyl isobutyl ketone, toluene, 2-nitropropane, xylene, isobutyl alcohol, n-butyl acetate.

It is preferred that the coated drug/resin complexes are coated in the range from about 40 to about 70% w/w drug/resin complex. More preferably, the drug/resin complex is coated in the range from about 45 to about 55% w/w drug/resin complex. Most preferably, the drug/resin complex is coated about 50% w/w drug/resin complex. Variation in the amount of coating and/or the use of coated/uncoated complex mixtures can be employed to selectively modify the dissolution profile as desired.

The average particle sizes of the non-hydrated coated and uncoated drug/resin complexes is about 60 to about 200 and about 60 to about 250 um, respectively. More preferably, average particle sizes of the coated drug/resin complexes is between about 70 and about 190 um, and most preferably about 70 to about 180 um. More preferably, average particle sizes of the uncoated drug/resin complexes is between about 55 and about 160 um, and most preferably about 60 to about 150 um. It is desirable that about 85%, preferably about 95%, and most preferably about 98% of the resin particles have sizes within the ranges set forth above. Adjustments within these ranges can be made to accommodate desired aesthetic qualities of the final formulation product. It is more preferable that the resin dextromethorphan complex have particle sizes within these ranges as well.

Preparation of the compositions as disclosed above leads to the reduction in the amount of dextromethorphan/ion exchange resin complexes required in a composition while still achieving a pharmaceutically effective activity level over a twelve hour period of time. While not intending to be limited by theory, it is believed that the inventors have discovered a way to use coatings in conjunction with increased drug loading to achieve plasma drug concentration levels that will provide relief for up to twelve hours. The amount of drug/resin in DELSYM DM dextromethorphan/resin compositions is estimated to be about 100 mg/5 ml, whereas the amount of drug/resin in the compositions of the present invention can be about 60 mg/ml.

Furthermore, unlike the drug/ion exchange resin preparations of the prior art, the sustained-release antitussive/ion exchange resin compositions of the present invention have been surprisingly and unexpectedly found to release up to about 90%, and even up to about 95% of an antitussive like dextromethorphan from the compositions over a twelve hour period. The bioavailability of dextromethorphan from the compositions of the present invention is high despite the strong bond between residual amounts of dextromethorphan and the ion exchange resin. If equivalent amounts of dextromethorphan/resin compositions of the present invention and DELSYM DM dextromethorphan/resin compositions are compared, the activity levels of the compositions of the present invention can be up to 15% more active than the DELSYM DM compositions. The foregoing assertions are evidenced by FIG. 1 which illustrates the in vitro dissolution profiles of the compositions of the present invention and DELSYM DM.

An additional advantages achieved by the compositions of the present invention, not available from other sustained-release dextromethorphan compositions relates to taste. Dextromethorphan is a drug which is unpleasant to take orally. Compositions, such as liquid suspension, comprising the drug/resin complexes of the present invention surprisingly and unexpectedly are pleasant tasting with good mouth-feel, even in the absence of sugars.

The drug/resin composition thus prepared may be stored for future use or formulated with conventional pharmaceutically acceptable carriers to prepare liquid compositions. The compositions according to this invention may, for example, take the form of liquid preparations such as suspensions, or solid preparations such as capsules, tablets, caplets, liquigells, powders.

The compositions may be formulated using conventional carriers or excipients and well established techniques. Without being limited thereto, such conventional carriers or excipients include diluents, binders and adhesives (i.e., cellulose derivatives and acrylic derivatives), lubricants (i.e., magnesium or calcium stearate, or vegetable oils, polyethylene glycols, talc, sodium lauryl sulphate, polyoxy ethylene monostearate), solubilizers, humectants, disintegrants, colorants, flavorings, preservatives, sweeteners and miscellaneous materials such as buffers and adsorbents in order to prepare a particular medicated composition.

Suitable thickeners include: tragacanth; xanthan gum; bentonite; acacia and lower alkyl ethers of cellulose (including the hydroxy and carboxy derivatives of the cellulose ethers). Preferably, tragacanth is used and incorporated in an amount of from about 0.1 to about 1.0% w/v of the composition, and more preferably about 0.5% w/v of the composition. Xanthan gum is used in the amount of from about 0.025 to about 0.5% w/v and preferably about 0.25% w/v.

The sustained-release antitussive/ion exchange resin compositions also include a humectant composition to also give the liquid greater viscosity and stability. Suitable humectants useful in the formulations of the present invention include glycerin, polyethylene glycol, propylene glycol and mixtures thereof. Preferably, polyethylene glycol is used and incorporated in an amount of from about 5 to about 20% w/v of the composition and preferably in an amount of from about 5 to about 15% w/v of the composition and most preferably in an amount of about 8% w/v of the composition.

The oral liquid compositions of the present invention will also comprise at least one and preferably two surfactants in amounts of up to about 5.0% w/v and preferably from about 0.02 to about 3.0% w/v of the total formulation. The surfactants useful in the preparation of the compositions of the present invention are generally organic materials which aid in the stabilization and dispersion of the ingredients in aqueous systems for a suitable homogenous composition. Preferably, the surfactants of choice are non-ionic surfactants such as poly(oxyethylene)(20)sorbitan monooleate and sorbitan monooleate. These are commercially known as Tweens and Spans and are produced in a wide variety of structures and molecular weights.

Whereas any one of a number of surfactants may be used, preferably a compound from the group comprising polysorbate copolymers (sorbitan-mono-9-octadecenoate-poly(oxy-1,2-ethanediyl)) is employed. This compound is also added and functions to keep any flavors and sweeteners homogeneously dissolved and dispersed in solution. It is also believed without being bound to any theory, that the polymers may provide a taste masking function as well by binding with the active.

Suitable polysorbates include polysorbate 20, polysorbate 40, polysorbate 80 and mixtures thereof Most preferably, polysorbate 80 is employed. The surfactant component will comprise from about 0.01 to about 2.0% w/v of the total composition and preferably will comprise about 0.1% w/v of the total weight of the composition.

A second emulsifier/surfactant useful in combination with polysorbates in the practice of the present invention may be employed and is preferably a poloxamer such as Poloxamer 407. Polyxamer 407 has an HLB (hydrophilic/lipophilic balance) of about 22 and is sold under the tradename Pluoronic-127 (BASF-Wyandotte; Parsippany, N.J.). The two surfactants can be employed in substantially equivalent amounts. For example, the Poloxamer 407 and polysorbate 80 may each be employed together at levels of approximately from about 0.02 to about 4.0% w/v of the total weight of the formulation.

Aqueous suspensions may be obtained by dispersing the drug/resin compositions in a suitable aqueous vehicle, optionally with the addition of suitable viscosity enhancing agent(s) (e.g., cellulose derivatives, xanthan gum, etc.). Non-aqueous suspensions may be obtained by dispersing the drug/resin compositions in a suitable non-aqueous based vehicle, optionally with the addition of suitable viscosity enhancing agent(s) (e.g., hydrogenated edible fats, aluminum stearate, etc.). Suitable non-aqueous vehicles include, for example, almond oil, arachis oil, soybean oil or fractionated vegetable oils such as fractionated coconut oil.

Preservatives useful in the present invention include, but are not limited to sodium benzoate, potassium sorbate, salts of edetate (also known as salts of ethylenediaminetetraacetic acid, or EDTA, such as disodium EDTA) and parabens (e.g., methyl, ethyl, propyl or butyl-hydroxybenzoates, etc.) or sorbic acid. The preservatives listed above are exemplary, but each preservative must be evaluated on an empirical basis, in each formulation, to assure the compatibility and efficacy of the preservative. Methods for evaluating the efficacy of preservatives in pharmaceutical formulations are known to those skilled in the art. Preferred preservatives are the paraben preservatives are methyl, ethyl, propyl, and butyl paraben. methyl and propyl paraben are most preferable. Preferably, both methyl and propyl paraben are present in the formulation in a ratio of methyl paraben to propyl paraben of from about 2.5:1 to about 7.5:1, preferably 3:1.

In the instance where auxiliary sweeteners are utilized, the present invention contemplates the inclusion of those sweeteners well known in the art, including both natural and artificial sweeteners. Thus, additional sweeteners may be chosen from the following non-limiting list:

A. Water-soluble sweetening agents such as monosaccharides, disaccharides and polysaccharides such as xylose, ribose, glucose, mannose, galactose, fructose, dextrose, sucrose, sugar, maltose, partially hydolyzed starch, or corn syrup solids and sugar alcohols such as sorbitol, xylitol, mannitol and mixtures thereof B. Sucralose.

C. Dipeptide based sweeteners such as L-aspartyl-phenylalanine methyl ester and materials described in U.S. Pat. No. 3,492,131 and the like.

In general, the amount of sweetener will vary with the desired amount of sweeteners selected for a particular liquid formulation. This amount will normally be 0.001 to about 90% by weight when using an easily extractable sweetener. The water-soluble sweeteners described in category A above, are preferably used in amounts of about 5 to about 70% by weight, and most preferably from about 10 to about 50% by weight of the final liquid composition. In contrast, the artificial sweeteners described in categories B and C are used in amounts of about 0.005 to about 5.0% and most preferably about 0.01 to about 2.5% by weight of the final liquid composition. These amounts are ordinarily necessary to achieve a desired level of sweetness independent from the flavor level achieved from flavor oils.

Suitable flavorings include both natural and artificial flavors, and mints such as peppermint, menthol, artificial vanilla, cinnamon, various fruit flavors, both individual and mixed, essential oils (i.e. thymol, eculyptol, menthol and methyl salicylate) and the like are contemplated. The amount of flavoring employed is normally a matter of preference subject to such factors as flavor type, individual flavor, and strength desired. Thus, the amount may be varied in order to obtain the result desired in the final product. Such variations are within the capabilities of those skilled in the art without the need for undue experimentation. The flavorings are generally utilized in amounts that will vary depending upon the individual flavor, and may, for example, range in amounts of about 0.01 to about 3% by weight of the final composition weight.

The colorants useful in the present invention, include the pigments such as titanium dioxide, that may be incorporated in amounts of up to about 1% by weight, and preferably up to about 0.6% by weight. Also, the colorants may include other dies suitable for food, drug and cosmetic applications, and known as D&C 10 and F.D. & C. dyes and the like. The materials acceptable for the foregoing spectrum of use are preferably water-soluble. Illustrative examples include indigoid die, known as F.D. & C. Blue No. 2, which is the disodium salt of 5,5'indigotindisulfonic acid. Similarly, the dye known as F.D. & C. Green No. 1, comprises a triphenylmethane dye and is the monosodium salt of 4-[4-Nethyl-p-sulfobenzylamino)diphenylmethylene]-[1-(N-ethyl-N-p-sulfoniumbenzyl)-2,5-cyclohexadienimine]. A full recitation of all F.D. & C. and D. & C. and their corresponding chemical structures may be found in the Kirk-Othmer Encyclopedia of Chemical Technology, in Volume 5, at Pages 857–884, which text is accordingly incorporated herein by reference.

Suitable oils and fats that are useable would include partially hydrogenated vegetable or animal fats, such as coconut oil, palm kernel oil, beef tallow, lard, and the like. These ingredients are generally utilized in amounts with respect to the comestible product of up to about 7.0% by weight, and preferably up to about 3.5% by weight of the final product.

Wetting agents also may be employed in the inventive compositions to facilitate the dispersion of any hydrophobic ingredients. The concentration of wetting agents in the composition should be selected to achieve optimum dispersion of the ingredient within the composition with the lowest feasible concentration of wetting agent. It should be appreciated that an excess concentration of wetting agent may cause the composition, as a syrup suspension, to flocculate. Those skilled in the art are well versed in suitable empirical methods to determine the appropriate wetting agents and concentrations to achieve optimum dispersion and avoid flocculation. Suitable wetting agents are listed in the U.S. Pharmacoepia XXI.

The invention further relates to methods of using the compositions in the treatment, management or mitigation of cough, cold, cold-like and/or flu symptoms and the discomfort, pain, fever and general malaise associated therewith.

The following examples are provided to more specifically teach and better define the sustained-release compositions of the present invention. They are for illustrative purposes only and it is realized that minor changes and variations can be made that are not disclosed therein. Such alternatives are still to be considered as falling within the spirit and scope of the present invention as recited by the claims that follow.

EXAMPLES

Example 1 Formulation

| Ingredient (and Test Standard) | Percentage Formula (%) Strength: 30 mg/5 mL |
|---|---|
| | Formula N° 1 |
| Dextromethorphan DRC-UNCOATED[1] Mfr | 0.276 |
| Dextromethorphan DRC50-COATED[2] Mfr | 0.970 |
| Tragacanth NF | 0.40 |
| Xanthan Gum NF | 0.10 |
| Sucralose | 0.02 |
| D&C Red N° 33 Mfr. | 0.001 |
| Xylitol NF | 15.00 |
| Polyethylene Glycol 600 NF | 8.00 |
| Methylparaben NF | 0.08 |
| Propylparaben NF | 0.05 |
| /-Menthol USP | 0.04 |
| Polysorbate 80 NF | 0.05 |
| Sorbitan Monooleate NF | 0.05 |
| Artificial Raspberry Flavour Mfr | 0.30 |
| Purified Water USP | qs |
| TOTAL | 100.00% |
| [1]Dextromethorphan DRC-UNCOATED | 0.276% |
| Consists of: | |
| Dextromethorphan (From Dextromethorphan Hydrobromide USP) | 0.132% |
| Polystyrene Sulfonate (From Sodium Polystyrene Sulfonate USP) | 0.144% |
| Equivalent to Dextromethorphan Hydrobromide USP | 9 mg/5 mL |
| [2]Dextromethorphan DRC50-COATED Consists of: | 0.970% |
| Dextromethorphan (From Dextromethorphan Hydrobromide USP) | 0.308% |
| Polystyrene Sulfonate (From Sodium Polystyrene Sulfonate USP) | 0.336% |
| SURELEASE (dry basis) | 0.326% |
| Colloidal silicon dioxide USP | ~0.001% |
| Equivalent to Dextromethorphan Hydrobromide USP | 21 mg/5 mL |
| [1+2]Label Claim (Equivalent to Dextromethorphan Hydrobromide USP) | 30 mg/5 mL |

Sustained Release Cough Syrup Preparation Procedure

Example 1 is prepared in accordance with the formulation set forth above, and the methods set forth in the specification. A dispersion of gums and stabilizers is prepared in a portion of water. The mixture is pasteurized by raising the temperature of the dispersion to between 60 and 90° C. for 0.5 to 2 hrs. To this dispersion preservatives and a portion of humectant and sweetener are added followed by the addition of the predispersed drug resin complexes in humectant and surfactants. After the addition of the remainder of the sweeteners and humectants, dyes and flavourings are added and the suspension is q.s ed with water.

Example 2 Formulation

Example 2 is prepared in a similar manner as Example 1.

| Ingredient (and Test Standard) | Percentage Formula (%) Strength: 30 mg/5 mL |
|---|---|
| | Formula N° 2 |
| Dextromethorphan DRC-UNCOATED[1] Mfr | 0.735 |
| Dextromethorphan DRC50-COATED[2] Mfr | 0.277 |
| Tragacanth NF | 0.40 |
| Xanthan Gum NF | 0.10 |
| Sucralose | 0.02 |
| D&C Red N° 33 Mfr. | 0.001 |
| Xylitol NF | 15.00 |
| Polyethylene Glycol 600 NF | 8.00 |
| Methylparaben NF | 0.08 |
| Propylparaben NF | 0.05 |
| /-Menthol USP | 0.04 |
| Polysorbate 80 NF | 0.05 |
| Sorbitan Monooleate NF | 0.05 |
| Artificial Raspberry Flavour Mfr | 0.30 |
| Purified Water USP | qs |
| TOTAL | 100.00% |
| 'Dextromethorphan DRC-UNCOATED Consists of: | 0.735% |
| Dextromethorphan (From Dextromethorphan Hydrobromide USP) | 0.352% |
| Polystyrene Sulfonate | 0.383% |

-continued

| Ingredient (and Test Standard) | Percentage Formula (%) Strength: 30 mg/5 mL |
|---|---|
| (From Sodium Polystyrene Sulfonate USP) | |
| Equivalent to Dextromethorphan Hydrobromide USP | 24 mg/5 mL |
| [2] Dextromethorphan DRC50-COATED Consists of: | 0.277% |
| Dextromethorphan | |
| (From Dextromethorphan Hydrobromide USP) | 0.088% |
| Polystyrene Sulfonate | |
| (From Sodium Polystyrene Sulfonate USP) | 0.096% |
| SURELEASE (fry basis) | 0.092% |
| Colloidal silicon dioxide USP | 0.001% |
| Equivalent to Dextromethorphan Hydrobromide USP | 6 mg/5 mL |
| [1+2]Label Claim (Equivalent to Dextromethorphan Hydrobromide USP | 30 mg/5 mL |

Example 3 Formulation

Example 3 is prepared in a similar manner as Example 1.

| Ingredient (and Test Standard) | Percentage Formula (%) Strength: 30 mg/5 mL |
|---|---|
| | Formula N° 3 |
| Dextromethorphan DRC-UNCOATED[1] Mfr | 0.436 |
| Dextromethorphan DRC50-COATED[2] Mfr | 0.797 |
| Tragacanth NF | 0.40 |
| Xanthan Gum NF | 0.10 |
| Sucralose | 0.02 |
| D&C Red N° 33 Mfr. | 0.001 |
| Xylitol NF | 15.00 |
| Polyethylene Glycol 600 NF | 8.00 |
| Methylparaben NF | 0.08 |
| Propylparaben NF | 0.05 |
| /-Menthol USP | 0.04 |
| Polysorbate 80 NF | 0.05 |
| Sorbitan Monooleate NF | 0.05 |
| Artificial Raspberry Flavour Mfr | 0.30 |
| Purified Water USP | qs |
| TOTAL | 100.00% |
| [1]Dextromethorphan DRC-UNCOATED Consists of: | 0.436% |
| Dextromethorphan | 0.198% |
| Polystyrene Sulfonate | 0.237% |
| Equivalent to Dextromethorphan Hydrobromide USP | 13.5 mg/5 mL |
| [2]Dextromethorphan DRC50-COATED Consists of: | 0.797% |
| Dextromethorphan | 0.242% |
| Polystyrene Sulfonate | 0.290% |
| SURELEASE (dry basis) | 0.264% |
| Colloidal silicon dioxide USP | ~0.001% |
| Equivalent to Dextromethorphan Hydrobromide USP | 16.5 mg/5 mL |
| [1+2]Label Claim (Equivalent to Dextromethorphan Hydrobromide USP | 30 mg/5 mL |

Example 4

In-vitro dissolution studies were carried out comparing the composition prepared according to Example 1 and 2 and DELSYM. The in-vitro dissolution test was carried out using USP apparatus II, 6 vessels with a stirring speed of 100 rpm. The dissolution medium was 750 g of 0.1 N HCl for the first hour and 250 g of sodium phosphate buffer was added after 1 hour to each vessel to give a sodium ion concentration of about 0.4 N and a pH of about 6.6. The dissolution media were maintained at 37° C. Samples were taken from each dissolution vessel at 0.5, 1, 2,3 4, 5, 7 and 12 hours with an automatic sampling device and analyzed by HPLC method.

The dissolution profiles of Example 1 and 2 and DELSYM are indicated by the results shown in Table 1 and graphically represented by FIG. 1.

TABLE 1

| | Percent of Dextromethorphan HBr H2O Release in Hours | | | | | | | | |
|---|---|---|---|---|---|---|---|---|---|
| Product | 0 | 0.5 | 1 | 2 | 3 | 4 | 5 | 7 | 12 |
| Example 1 | 0 | 0.34 | 0.42 | 0.65 | 0.73 | 0.80 | 0.84 | 0.90 | 0.93 |
| Example 2 | 0 | 0.52 | 0.62 | 0.84 | 0.84 | 0.87 | 0.88 | 0.90 | 0.91 |
| DELSYM | 0 | 0.42 | 0.48 | 0.71 | 0.73 | 0.75 | 0.77 | 0.79 | 0.82 |

What is claimed is:

1. A sustained release pharmaceutical composition comprising:

a drug/resin complex including a coated portion that comprises about 20 to about 80% of the drug/resin complex, and an uncoated portion; wherein the coated portion is coated with a water permeable diffusion barrier in an amount from about 33 to about 70% w/w of the coated portion and both the coated and uncoated portions include the same drug in an amount from about 25 to about 75% w/w of the drug/resin complex.

2. The sustained release pharmaceutical composition according to claim 1 wherein the coating comprises a mixture of ethyl cellulose and water soluble polymers.

3. The sustained release pharmaceutical composition according to claim 1 wherein the particle size of the coated drug/resin complex is about 20 to about 300 um and the particle size of the uncoated drug/resin complex is about 20 to about 250 um.

4. The sustained release pharmaceutical composition according to claim 1 wherein the drug is an antitussive.

5. The sustained release pharmaceutical composition according to claim 4 wherein the antitussive is selected from the group consisting of dextromethorphan, diphenhydramine, caramiphen, carbapentane, ethylmorphine, noscapine and codeine.

6. The sustained release pharmaceutical composition according to claim 5 wherein the antitussive is dextromethorphan.

7. The sustained release pharmaceutical composition according to claim 4 further comprising at least one of an antihistamine, analgesic, antiinflammatory, antipyretic or a sympathomimetic drug.

8. The sustained release pharmaceutical composition according to claim 1 wherein the composition is capable of releasing about 90% of the drug in twelve hours.

9. A method of using the composition of claim 1 in the treatment, management or mitigation of symptoms selected from the groups consisting of cough, cold, coldlike and/or flu symptoms and the discomfort, pain, allergy, fever and general malaise associated therewith.

10. A pharmaceutical composition comprising a dextromethorphan/ion exchange resin complex having a ratio of dextromethorphan to ion exchange resin of about 1:2 to about 2:1 and about 40% to about 60% of the resin complex is coated with a water permeable diffusion barrier in an amount from about 33 to about 70% w/w of the coated complex.

11. The pharmaceutical composition according to claim 10 wherein the coating comprises a mixture of ethyl cellulose and water soluble polymers.

12. The sustained release pharmaceutical composition according to claim 10 wherein the particle size of the coated dextromethorphan/resin complex is about 20 to about 300 um and the particle size of the uncoated dextromethorphan/resin complex is about 20 to about 250 um.

13. The pharmaceutical composition according to claim 10 further comprising at least one of an antihistamine, analgesic, antiinflammatory, antipyretic or a sympathomimetic drug.

14. The pharmaceutical composition according to claim 10 wherein the composition is capable of releasing about 90% of the dextromethorphan in twelve hours.

15. A method of using the composition of claim 10 in the treatment, management or mitigation of symptoms selected from the groups consisting of cough, cold, coldlike and/or flu symptoms and the discomfort, pain, allergy, fever and general malaise associated therewith.

16. A composition consisting essentially of:

| Ingredient (and Test Standard) | Percentage Formula (%) Strength: 30 mg/5 mL |
| --- | --- |
| Dextromethorphan DRC-UNCOATED[1] Mfr | 0.436 |
| Dextromethorphan DRC50-COATED[2] Mfr | 0.797 |
| Tragacanth NF | 0.40 |
| Xanthan Gum NF | 0.10 |
| Sucralose | 0.02 |
| D&C Red N° 33 Mfr. | 0.001 |
| Xylitol NF | 15.00 |
| Polyethylene Glycol 600 NF | 8.00 |
| Methylparaben NF | 0.08 |
| Propylparaben NF | 0.05 |
| /-Menthol USP | 0.04 |
| Polysorbate 80 NF | 0.05 |
| Sorbitan Monooleate NF | 0.05 |
| Artificial Raspberry Flavour Mfr | 0.30 |
| Purified Water USP | qs |
| TOTAL | 100.00% |
| [1]Dextromethorphan DRC-UNCOATED Consists of: | 0.436% |
| Dextromethorphan | 0.198% |
| Polystyrene Sulfonate | 0.237% |
| Equivalent to Dextromethorphan Hydrobromide USP | 13.5 mg/5 mL |
| [2]Dextromethorphan DRC50-COATED Consists of: | 0.797% |
| Dextromethorphan | 0.242% |
| Polystyrene Sulfonate | 0.290% |
| Surelease (dry basis) | 0.264% |
| Colloidal silicon dioxide USP | ~0.001% |
| Equivalent to Dextro methorphan Hydrobromide USP | 16.5 mg/5 mL |
| [1+2]Label Claim (Equivalent to Dextromethorphan Hydrobromide USP | 30 mg/5 mL |

17. The composition of claim 16 further comprising at least one of an antitussive, antihistamine, analgesic, antiinflammatory, antipyretic, or a sympathomimetic drug.

18. A method of using the composition of claim 16 in the treatment, management or mitigation of symptoms selected from the group consisting of: cough, cold, cold-like and/or flu symptoms and the discomfort, pain, allergy, fever and general malaise associated therewith.

* * * * *